United States Patent [19]

Levy

[11] Patent Number: 4,824,369

[45] Date of Patent: Apr. 25, 1989

[54] MANUALLY OPERATED ENDODONTIC INSTRUMENT

[76] Inventor: Guy Levy, 49, rue Croix de Regnier, F-13004 Marseille, France

[21] Appl. No.: 48,685

[22] Filed: May 12, 1987

[51] Int. Cl.$^4$ .............................................. A61C 5/02
[52] U.S. Cl. ................................................ 433/102
[58] Field of Search ........................ 433/102, 146, 141

[56] References Cited

U.S. PATENT DOCUMENTS 3,247,594  4/1966  Nosonowitz ...................... 433/102
4,643,674  2/1987  Zdorsky .............................. 433/102

FOREIGN PATENT DOCUMENTS 1044  3/1979  European Pat. Off. ............ 433/147

Primary Examiner—Robert Peshock
Attorney, Agent, or Firm—Spensley Horn Jubas & Lubitz

[57] ABSTRACT

A manually operated endodontic instrument composed of: an endodontic file; and a handle to which the file is immovably secured, the handle being formed to be gripped between the thumb and the index finger, having a longitudinal axis and an outer surface and including a central, longitudinally extending portion and first and second bulbous portions each joined to a respective longitudinal end of the central portion and each projecting laterally beyond the central portion, the handle being provided, at its outer surface, with at least two circumferentially spaced recesses extending longitudinally along at least part of the central portion.

8 Claims, 1 Drawing Sheet

MANUALLY OPERATED ENDODONTIC INSTRUMENT

BACKGROUND OF THE INVENTION

The present invention relates to handles for manually operated endodontic instruments.

Endodontic instruments are those which are used to perform the various phases of endodontic, or root canal, treatment. The first steps in a root canal treatment involve opening the canal, followed by a reaming, or filing, operation to increase the canal diameter.

While power driven instruments have been developed, and are used, for these operations, there remains a place in the field for manually operated instruments.

The successful use of endodontic instruments, and particularly manually operated instruments, depends to a substantial degree on the skill of the practitioner and his ability to precisely control the movements of the instrument. In this connection, the handle of the instrument is of considerable importance because of its influence on the precision with which the practitioner can control the movements of the element acting in the root canal, which element is generally a very thin file. Such file most commonly has a helical structure. For example, a Kerr file is constituted by a steel wire which is tapered toward its free end and is twisted about its axis to form a helical structure. The initial cross section of the wire is generally triangular or square. Other file types, such as the Hedstrem file, are also known.

The canal in a tooth is initially a very small diameter and often follows a curved path. In order to open such a canal by means of a file, the practitioner must apply to the file a movement which combines pushing and rotational components to permit the file to penetrate into, and advance along, the path of the canal.

In order to subsequently enlarge the canal, its walls must be reamed or filed. The movements required vary from one file type to another. Thus, in the case of a Hedstrem file, movements including rotation and pulling components must be imposed in order to cause the file blades to cut into the tooth dentine, and a pulling force must be applied to extract the cuttings, or filings. In the case of a Kerr file, a longitudinal back and forth filing movement is appropriate to cause the teeth or blades of the file to rub against the canal walls.

The effectiveness of such instruments is dependent to a substantial extent on their handle, because the shape of the handle determines the ease with which the practitioner can produce, and control, the various types of movements, dictated by the conditions encountered within the canal. Thus, the handle, which is normally grasped between the thumb and index finger, must be gripped so that, in certain circumstances, rotation of the file is prevented, and, in other circumstances, a controlled rotation is imparted thereto.

SUMMARY OF THE INVENTION

It is an object of the present invention to provide a novel handle structure for manually operated endodontic instruments which permits any desired movement, or combination of movements, to be easily imparted to the endodontic file.

Another object of the invention is to provide a novel endodontic instrument handle which can be held comfortably between the thumb and index finger.

Yet another object of the invention is to provide an endodontic instrument handle via which both pushing and pulling forces can be transmitted.

Yet another object of the invention is to provide an endodontic instrument handle which can be selectively gripped to either prevent rotation of the attached file or permit a controlled rotation thereof.

The above and other objects are achieved, according to the invention, by a manually operated endodontic instrument comprising: an endodontic file; and a handle to which the file is immovably secured, the handle being formed to be gripped between the thumb and the index finger, having a longitudinal axis and an outer surface and including a central, longitudinally extending portion and first and second bulbous portions each joined to a respective longitudinal end of the central portion and each projecting laterally beyond the central portion, the handle being provided, at its outer surface, with at least two circumferentially spaced recesses extending longitudinally along at least part of the central portion.

DESCRIPTION OF THE PREFERRED EMBODIMENTS

As is shown in the Figures, a handle according to the present invention has a basically circular cross section throughout and is composed of: a central shank portion 2 which is slightly constricted at its center, i.e. the diameter in plane C—C is slightly less than that at the ends of portion 2; and enlarged, or bulbous, end portions 4 and 6 which merge into portion 2 via rounded surface regions. Portion 4 is axially shorter and radially larger than portion 6. Typical dimensions for the handle, in millimeters, are indicated on the various Figures.

The outer surface of the handle is provided with two elongate indentations 8 which extend along portion 2, and overlap slightly into portions 4 and 6, each indentation having a slightly concave surface.

Figure 1:
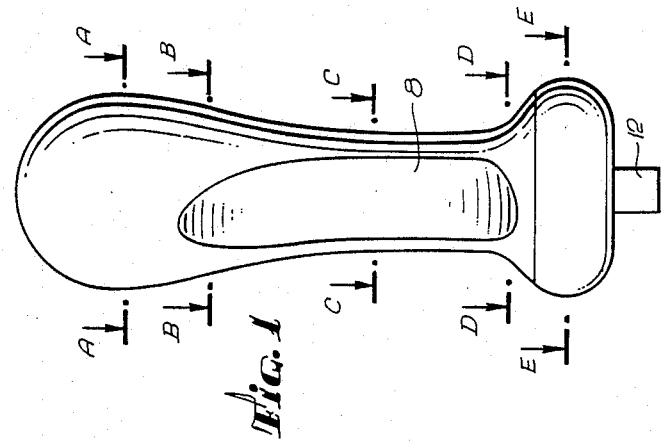
FIG. 1 is a side elevational view of a preferred embodiment of a handle according to the present invention.

The two indentations 8 are disposed in mirror symmetry to a plane 10 passing through the center axis of the handle, plane 10 being the plane of FIG. 1. However, recesses 8 are not diametrically opposite one another, but rather extend generally at an acute angle to plane 10.

Figure 2:
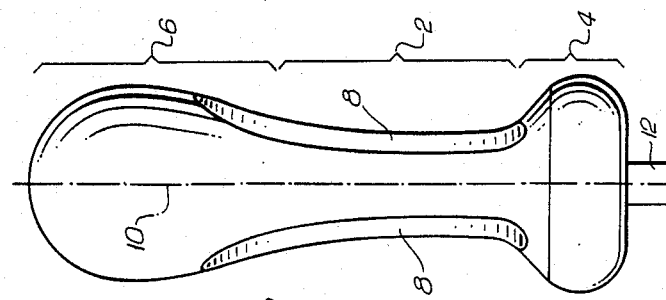
FIG. 2 is a front elevational view of the handle of FIG. 1.
Figure 3:
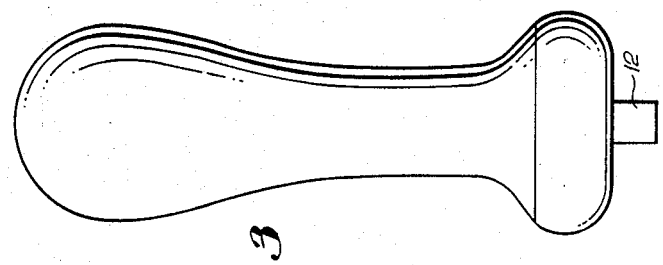
FIG. 3 is a rear elevational view of the handle of FIG. 1.
Figure 4:
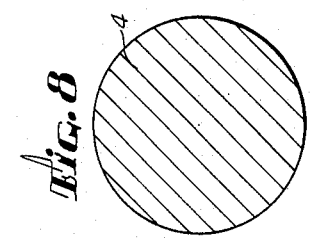
FIGS. 4-8 are cross-sectional views taken along lines A—A, B—B, C—C, D—D and E—E, respectively, of FIGS. 1-3.
Figure 6:
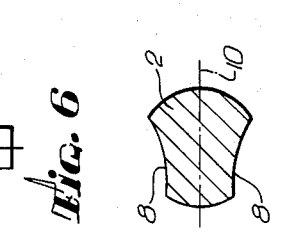
Figure 7:
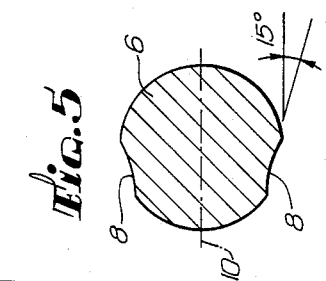
Figure 8:
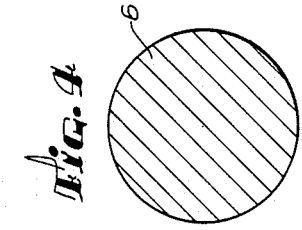

Recesses 8 are concave in planes perpendicular to the longitudinal axis of the handle (see FIGS. 5, 6 and 7), and in planes containing the longitudinal axis of the handle. This is apparent from FIG. 2, as well as from a comparison of FIGS. 5, 6 and 7. Thus, the recesses are closest to one another in plane C—C, and are furthest apart at their ends, corresponding essentially to planes B—B and D—D.

Typical embodiments of the invention are dimensioned so that the length of the handle portion contacted by the thumb and index finger, i.e. approximately between planes A—A and D—D, is of the order of 10 mm, and the diameter of the cylindrical basic cross section of the handle, i.e. excluding recesses 8, varies between a minimum of about 3 mm, approximately at plane C—C, and a maximum of about 5 mm, at plane E—E.

The radius of curvature of recesses 8 in planes perpendicular to the longitudinal axis of the handle is selected to match the curvature of the thumb and index finger tips each engage therein.

According to an alternative embodiment of the invention, more than two recesses 8 can be provided. For example, three of four recesses could be provided, and could be equispaced about the longitudinal axis of the handle.

Figure 5:
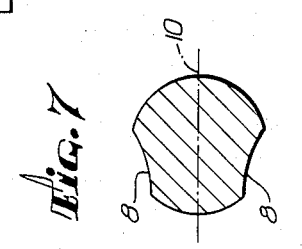

As indicated in FIG. 5, the inclination of each recess to plane 10, in the illustrated embodiment, could be such that a plane tangent to the center of each recess forms an angle of the order of 15° with plane 10.

The handle carries, at its lower end, a file 12 which is immobilized relative to the handle. Preferably, file 12 is inserted in such a manner as to permit it to be removed and replaced by a different file.

In use, the handle according to the invention is gripped between the thumb and index finger, with the tips of the thumb and index finger bearing against the upper surface of rounded portion 4. This permits longitudinal pushing movements to be transmitted to file 12. Correspondingly, rounded portion 6 at the upper end of the handle facilitates the transmission of longitudinal pulling forces to the instrument.

When it is desired to prevent rotation of file 12, the thumb and index finger are placed to engage in recesses 8, thereby preventing any rotation of the handle, and therefore of file 12. If a controlled rotational movement is to be imparted to file 12, the handle is gripped so that the thumb and index finger contact the surface portions of circular cross section at the front and rear sides of the handle. Thus, by a simple manipulation, the user can easily proceed from an operation in which rotation is to be blocked to one in which a controlled degree of rotation is imparted. In either position, the enlarged portions 4 and 6 assure effective transmission of both pushing and pulling forces in the longitudinal direction of the instrument.

The invention now being fully described, it will be apparent to one of ordinary skill in the art that many changes and modifications can be made thereto without departing from the spirit or scope of the invention as set forth herein.

What is claimed is:

1. A manually operated endodontic instrument comprising: an endodontic file; and a handle to which said file is immovably secured, said handle being formed to be gripped between the thumb and the index finger, having a longitudinal axis and an outer surface and including a central, longitudinally extending portion and first and second bulbous portions each joined to a respective longitudinal end of said central portion and each projecting laterally beyond said central portion, said handle being provided, at its outer surface, with at least two circumferentially spaced recesses extending longitudinally along at least part of said central portion, and wherein: said handle has a length of at least 10 mm; said recesses are formed such that, in the direction perpendicular to the longitudinal axis, said recesses have a minimum spacing which is less than one-half the maximum dimension of said handle; said handle is configured and dimensioned so that when gripped, the tips of the thumb and index finger bear against that one of said bulbous portions which is at the end of said handle to which said file is secured and portions of the thumb and index finger spaced from the tips thereof bear against the other one of said bulbous portions; said outer surface of said handle has, in the direction of the longitudinal axis of said handle, a concave gradual curvature at each location where a respective bulbous portion is joined to said central portion; and said recesses are oriented relative to one another so that the tangents to the centers of the recesses, which tangents lie in a plane perpendicular to the longitudinal axis of said handle, form an acute angle of greater than 0° with one another.

2. An instrument as defined in claim 1 wherein each said recess has a concave form in planes perpendicular to the longitudinal axis of said handle.

3. An instrument as defined in claim 2 wherein each said recess extends, in the direction of the longitudinal axis of said handle, over the entire length of said central portion and partially along each of said bulbous portions.

4. An instrument as defined in claim 1 wherein the acute angle has a magnitude of the order of 30°.

5. An instrument as defined in claim 1 wherein said outer surface has, outside of the regions of said recesses, a convex curvature in planes perpendicular to the longitudinal axis of said handle.

6. An instrument as defined in claim 5 wherein the convex curvature is circular.

7. An instrument as defined in claim 1 wherein said bulbous portions constitute respective longitudinal ends of said handle.

8. An instrument as defined in claim 1 wherein each said recess extends, in the direction of the longitudinal axis of said handle, over the entire length of said central portion and partially along each of said bulbous portions.

* * * * *